(12) United States Patent
Vazquez

(10) Patent No.: US 6,547,560 B1
(45) Date of Patent: Apr. 15, 2003

(54) ORTHODONTIC BITE JUMPING DEVICE WITH A TELESCOPING LIMITING ASSEMBLY

(76) Inventor: Juan F. Vazquez, 2110 Sylvester Rd., #3, Lakeland, FL (US) 33803-3555

( * ) Notice: Subject to any disclaimer, the term of this patent is extended or adjusted under 35 U.S.C. 154(b) by 0 days.

(21) Appl. No.: 09/967,706

(22) Filed: Oct. 1, 2001

(51) Int. Cl.[7] ................................................. A61C 7/00
(52) U.S. Cl. ....................................................... 433/19
(58) Field of Search ............................. 433/19, 18, 21, 433/22

(56) References Cited

U.S. PATENT DOCUMENTS 5,738,514 A * 4/1998 DeVincenzo et al. ......... 433/19
5,879,157 A * 3/1999 Scheu .......................... 433/19

* cited by examiner

Primary Examiner—Kevin Shaver
Assistant Examiner—Melba Bumgarner
(74) Attorney, Agent, or Firm—George A. Bode; Lisa D. Velez; Bode & Associates

(57) ABSTRACT

An orthodontic bite jumping device for use in the treatment of malocclusion or overbite, having a telescoping limiting assembly to prevent an inner cylindrical member from being completely pulled-out of an outer tube as a patient opens their mouth very wide. The outer tube is adapted to be mounted to an upper jaw or maxilla and the inner cylindrical member is concentrically disposed in the outer tube and adapted to be mounted to a lower jaw or mandible. The telescoping limiting assembly limits the distance the inner cylindrical member can slide out of the outer tube via a pair of notches and an L-shaped resilient lever arm. The first notch is formed in close proximity to a free end of the outer tube. The second notch is formed in close proximity to a free end of the inner cylindrical member and has a rear blocking surface and a forward descending slope or ramped surface to a bottom of the rear blocking surface. In operation, the L-shaped resilient lever arm tracks the forward descending slope or ramped surface in and out of the second notch.

20 Claims, 4 Drawing Sheets

ORTHODONTIC BITE JUMPING DEVICE WITH A TELESCOPING LIMITING ASSEMBLY

BACKGROUND OF THE INVENTION

1. Field of the Invention

The present invention relates to orthodontic bite jumping devices and, more particularly, to an orthodontic bite jumping device, such as for use in the treatment of malocclusion or overbite, having a telescoping limiting assembly to prevent the inner cylindrical member from being completely pulled-out of the outer tube.

2. General Background

The Herbst Appliance or other similar orthodontic bite jumping devices were successful in the treatment of malocclusion or overbite, as described in "The mechanism of Class II correction in Herbst appliance treatment"; by Hans Pancherz, DDS; Am. J. Orthod.; Vol. 82; No. 2; August 1982; (104–107). However, it was determined that in some instances, when the mouth was opened wide such as the involuntary response during yarning, the upper and lower telescoping tubes became displaced and disconnected. In other words, the inner member would sometime become completely pulled out of the outer tube, as described in "The Bonded Herbst Appliance"; by Raymond P. Howe, DDS, MS; J. Clin. Orthod.; October, 1982 (663–667).

Thus, several attempts have been made to prevent the inner member from becoming completely pulled out of the outer tube. For example, U.S. Pat. No. , 5,738,514, issued to DeVincenzo et al., entitled "RESILIENTLY EXPANDABLE ORTHODONTIC DEVICE" discloses an orthodontic appliance having a pair of cooperating telescoping cylinders and a stop means using a projection to prevent the disconnection of the'telescoping cylinders. Another example is described in U.S. Pat. No. 5,879,157, issued to Scheu, entitled "HERBST MECHANISM" which uses a guiding pin positioned in a guiding slot.

Other orthodontic device in the art includes Italian Patent No. 335395, which discloses anorthodontic device having a means for expanding which includes a bar connecting the brace wire sets and ratcheting elements connected to the upper wire set.

U.S. Pat. No. 3,798,773 issued to M. E. Northcutt, entitled "DEVICE FOR IMPROVING THE ALIGNMENT OF THE UPPER AND LOWER SETS OF TEETH WITH EACH OTHER" discloses a device for realigning teeth which includes a pair of spring arrangements which move the upper row of teeth rearwardly and the lower teeth forward each time he closes his mouth utilizing the vertical closure force of his masseter muscle. The device comprises telescoping tubes secured to brace wires. The tubes are urged apart by a spring therein, the spring bearing against a cylinder connected to a ball in a socket connected to a fitting. A set screw enables a cylinder to be adjusted so that the device can be used on all patients.

U.S. Pat. No. 5,678,990 issued to F. Rosenberg discloses an apparatus for cushioning bite jumping and the correction of Class II malocclusions wherein, the upper and lower sets of teeth are connected by a piston and cylinder having a chamber to accommodate a spring therebetween.

As will be seen more fully below, the present invention is substantially different in structure, methodology and approach from that of the prior orthodontic bite jumping devices.

SUMMARY OF THE PRESENT INVENTION

The preferred embodiment of the orthodontic bite jumping device of the present invention solves the aforementioned problems in a straight forward and simple manner.

Broadly, what is provided is an orthodontic bite jumping device comprising: an outer tube having one end adapted to be mounted to an upper jaw; an inner cylindrical member concentrically disposed in said outer tube and adapted to be mounted to a lower jaw; a telescoping limiting assembly which limits the distance said inner cylindrical member can slide out of said outer tube, said telescoping limiting assembly includes: a first notch formed in close proximity to a free end of said outer tube; a second notch formed in close proximity to a free end of said inner cylindrical member and having a rear blocking surface and a forward descending slope or ramped surface sloped to a bottom of said rear blocking surface; and, a L-shaped resilient lever arm which tracks along a top of said inner cylindrical member in the first notch and tracks along the forward descending slope or ramped surface as a portion of said inner cylindrical member slides out of said outer tube.

Additionally, the present invention contemplates an artificial orthodontic joint for connection between a maxilla and a mandible comprising: a telescopic tube having one end adapted to be mounted to said maxilla; a first notch formed in close proximity to a free end of said telescopic tube; a plunger cylindrical member concentrically disposed in said telescopic tube and adapted to be mounted to said mandible; a second notch formed in close proximity to a free end of said plunger cylindrical member and having a rear tracking limiting surface and a forward descending slope or ramped surface sloped to and ending at a bottom of said rear tracking limiting surface; and a L-shaped resilient lever arm coupled to said outer tube and which tracks along a top of said plunger cylindrical member in the first notch and along the forward descending slope or ramped surface The present invention further contemplates a L-shaped resilient lever arm that resiliently tracks along the forward descending slope or ramped surface out of the second notch as a portion of the plunger or inner cylindrical member slides into said telescopic or outer tube.

Furthermore, the present invention contemplates an artificial orthodontic joint for connection between a maxilla and a mandible comprising: a telescopic tube having one end adapted to be mounted to said mandible; and a plunger cylindrical member concentrically disposed in said telescopic tube and adapted to be mounted to said maxilla.

In view of the above an object of the present invention is to provide an orthodontic bite jumping device for use in the treatment of malocclusion or overbite, which has a telescoping limiting assembly to prevent the, inner cylindrical member from being completely pulled-out of the central bore of the outer tube.

Another object of the present invention is to provide an orthodontic bite jumping device which includes a telescoping limiting assembly having a ramped notch to dampen the effect of the inner cylindrical member upon closure and which permits a gradual transition out of the ramped notch.

A further object of the present invention is to provide an orthodontic bite jumping device having a L-shaped resilient lever arm which is removable.

A still further object of the present invention is to provide an orthodontic bite jumping device having a L-shaped resilient lever arm which is permanently affixed to the outer tube.

A still further object of the present invention is to provide an orthodontic bite jumping device having telescoping limiting assembly which is constructed and arranged to provide a smooth transition in and out of a limiting position wherein such limiting position prevents the inner cylindrical member from being completely pulled-out of the central bore of the outer tube.

In view of the above, a feature of the present invention is to provide an orthodontic bite jumping device which borrows from the Herbst appliance design to create an artificial joint between the maxilla and the mandible while preventing the outer tube and the inner cylindrical member from being disconnected or disengaged.

Another feature of the present invention is to provide an orthodontic bite jumping device which is simple to use.

A further feature of the present invention is to provide an orthodontic bite jumping device which includes a telescoping limiting assembly which is relatively simple structurally and thus simple to manufacture.

The above and other objects and features of the present invention will become apparent from the drawings, the description given herein, and the appended claims.

BRIEF DESCRIPTION OF THE DRAWING

For a further understanding of the nature and objects of the present invention, reference should be had to the following description taken in conjunction with the accompanying drawings in which like parts are given like reference numerals and, wherein.

DETAILED DESCRIPTION OF THE PREFERRED EMBODIMENT

Figure 1:
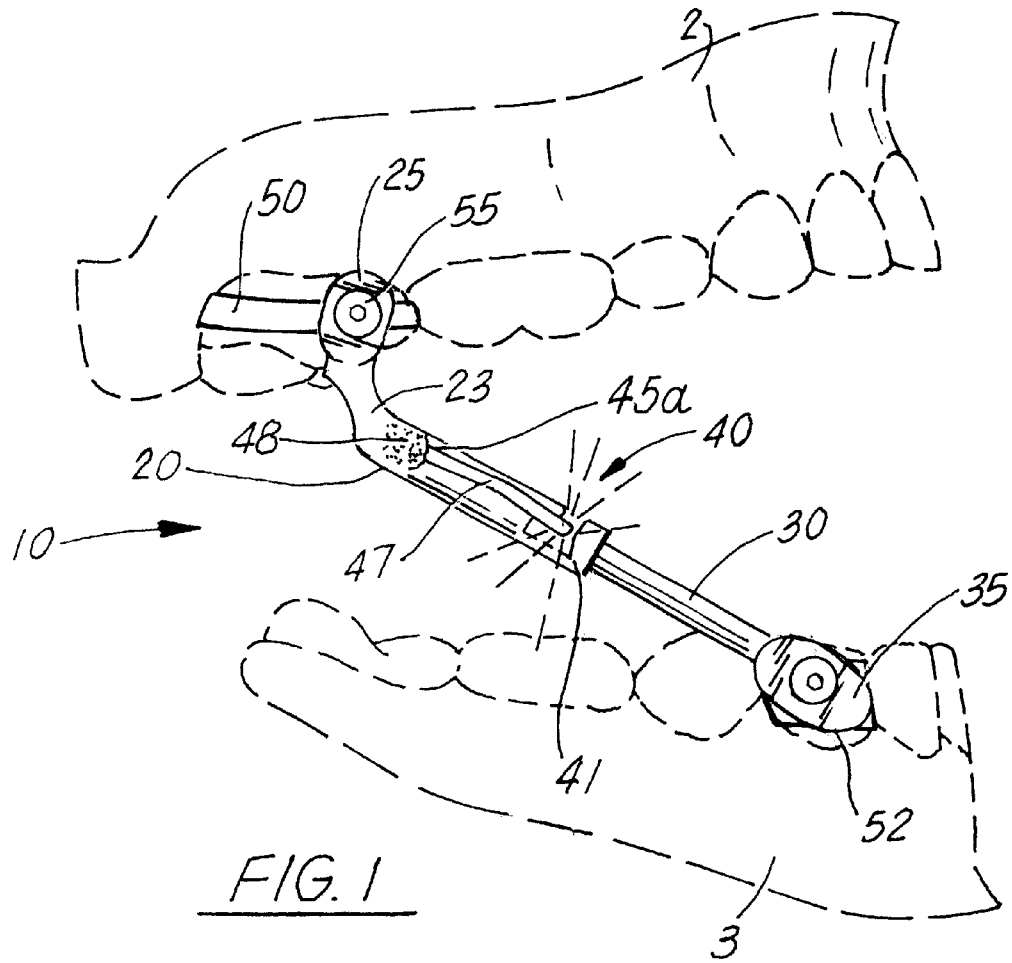
FIG. 1 illustrates a perspective view of the orthodontic bite jumping device of the present invention installed on tooth bands with the teeth in occlusion or opened and the device in the limiting or locked position.
Figure 2:
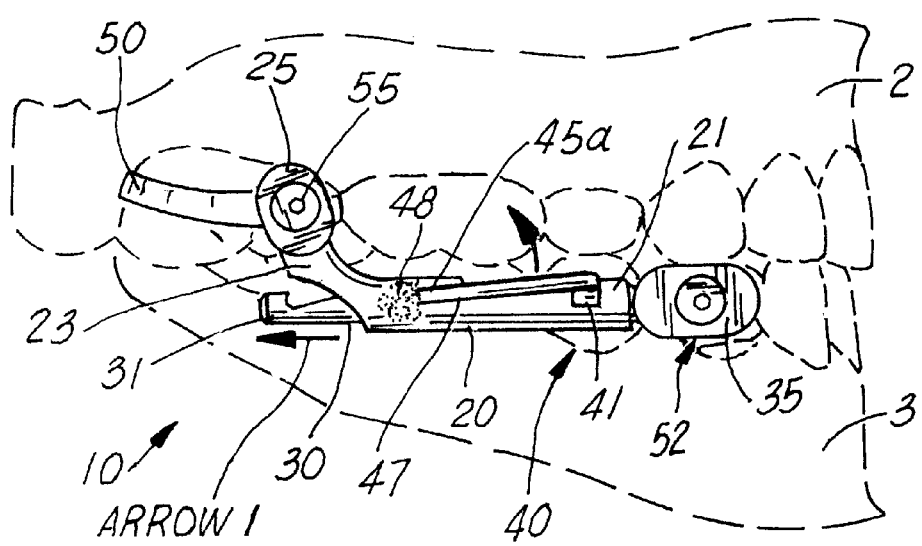
FIG. 2 illustrates a perspective view of the orthodontic bite jumping device of the embodiment of FIG. 1 with the jaw closed.

Referring now to the drawings and in particular FIGS. 1–2, the orthodontic bite jumping device of the present invention of the present invention is generally referenced by the numeral 10. As will be seen from the description below, the orthodontic bite jumping device 10 of the present invention borrows from the Herbst design to create an artificial joint between the maxilla (upper jaw) 2 and the mandible (lower jaw) 3 while overcoming the disadvantages thereof. The orthodontic bite jumping device 10 comprises a telescopic or outer tube 20 and a plunger or inner cylindrical member 30. The telescopic or outer tube 20 and a plunger or inner cylindrical member 30 are generally cylindrically shaped and have longitudinal axes which are adapted to be aligned when the inner cylindrical member 30 is concentric with the outer tube 20.

Referring also to FIGS. 3–8, the telescopic or outer tube 20 has fixed to one free end thereof a ring or eyelet 25 via connecting arm 23 which displaces the ring or eyelet 25 approximately 45 degrees with respect to the longitudinal axis of telescopic or outer tube 20. The plunger or inner cylindrical member 30 has fixed to one free end a ring or eyelet 35 wherein the ring or eyelet 35 is substantially aligned with the longitudinal axis of the plunger or inner cylindrical member 30. The rings or eyelets 25 and 35 have thin profiles or widths.

Figure 8:
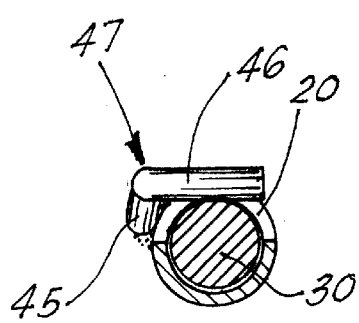
FIG. 8 illustrates a cross sectional view along the plane 5—5 of FIG. 5.

The orthodontic bite jumping device 10 includes a telescoping limiting assembly 40 which limits the distance the telescopic tube 20 can slide or track along the plunger cylindrical member 30 to prevent the telescopic tube 20 from becoming disconnected, disengaged or pulled off of the plunger cylindrical member 30. The telescoping limiting assembly 40 includes a pair of notches 41a and 41b formed in close proximity to the free ends 21 and 31, respectively, of the telescopic tube 20 and the plunger cylindrical member 30, respectively. The telescoping limiting assembly 40 further includes a L-shaped resilient lever arm 47 which rides or tracks along the top of the plunger cylindrical member 30 in the notch 41a, as best seen in FIG. 8.

The notch 41b has a rear tracking limiting surface 42 and a forward descending slope or ramped surface 43 sloping to and ending at a bottom of the rear tracking limiting surface 42. The L-shaped resilient lever arm 47 rides or tracks along the forward sloped or ramped surface 43 of notch 41b and resiliently adapted to the slope or ramped contour thereof while moving freely in notch 41a until the L-shaped resilient lever arm 47 engages the rear tracking limiting surface 42. When the L-shaped resilient lever arm 47 engages the rear tracking limiting surface 42, the L-shaped resilient lever arm 47 is substantially at the lower end of notch 41a and notch 41b. Thus, the plunger cylindrical member 30 is prevented from any further sliding movement in the direction of ARROW 1. Thus, the plunger cylindrical member 30 is prevented from being completely pulled out from the central bore 20a of the telescopic tube 20.

The slope or ramped contour of notch 41b enables the L-shaped resilient lever arm 47 to be easily ramped upward so that the telescopic tube 20 and the plunger cylindrical member 30 can collapse as the plunger cylindrical member 30 slides or tracks in a direction opposite that of ARROW 1.

The tension felt is slightly more than during the ramping force exerted by the L-shaped resilient lever arm 47 sliding along the plunger cylindrical member 30. Thus, the patient would be required to apply a slightly greater force when closing their mouth so that the L-shaped resilient lever arm 47 can be ramped up and out of notch 41b.

Figure 1A:
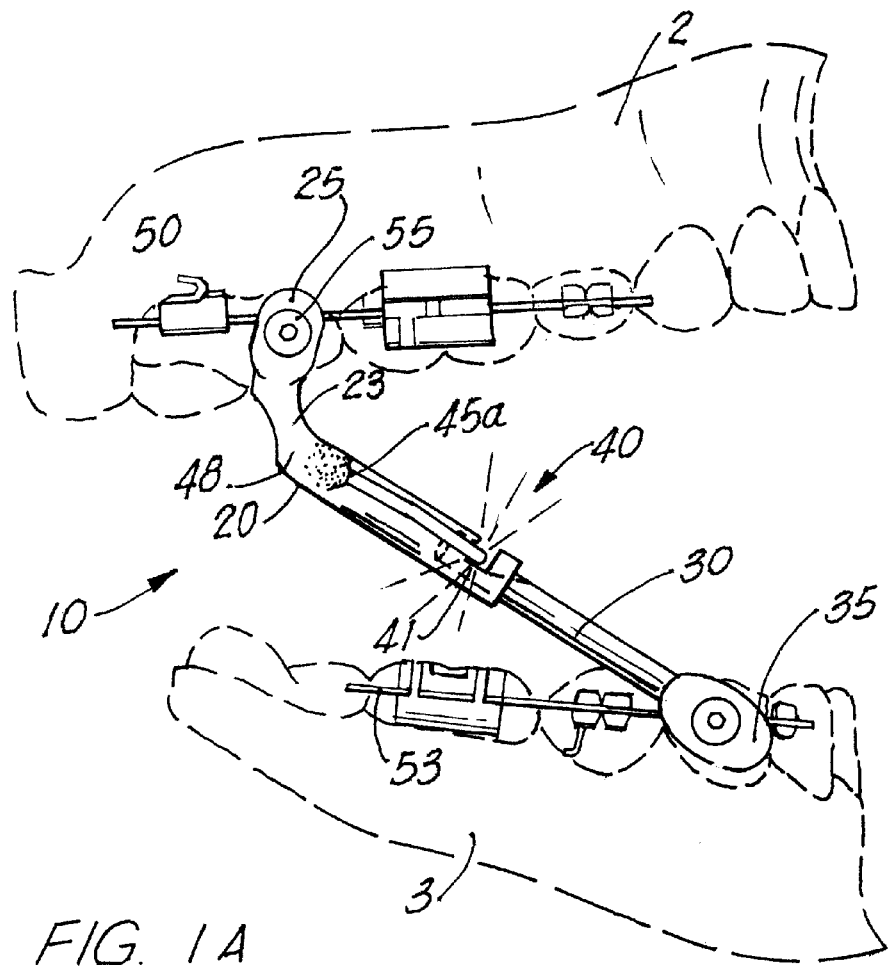
FIG. 1A illustrates a perspective view of the orthodontic bite jumping device of the present invention installed on brace wires with the teeth in occlusion or opened and the device in the limiting or locked position.
Figure 2A:
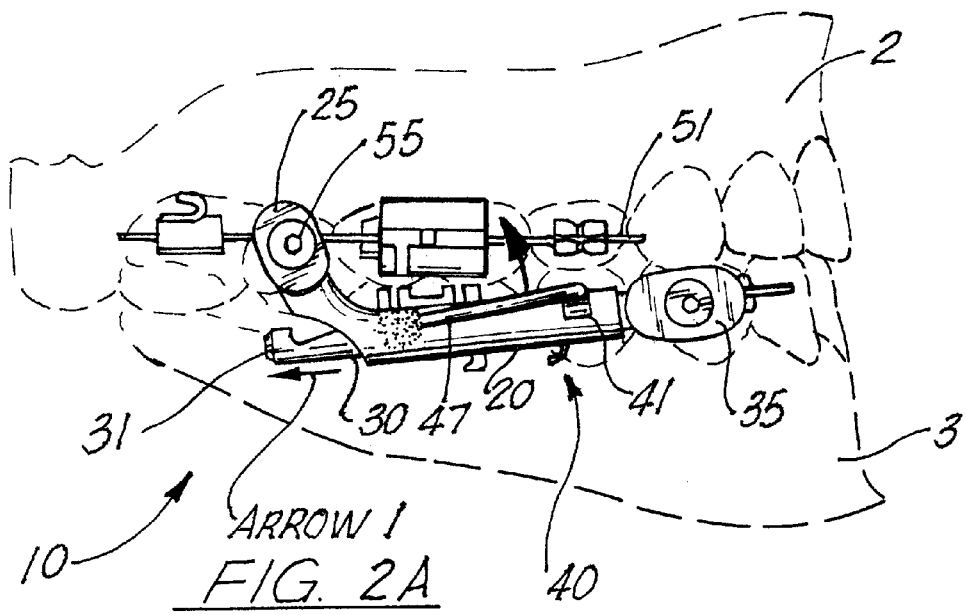
FIG. 2A illustrates a perspective view of the orthodontic bite jumping device of the embodiment of FIG. 1A with the jaw closed.
Figure 3:
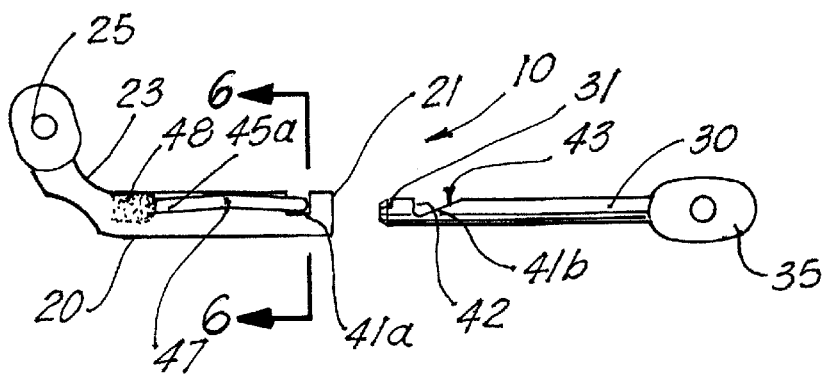
FIG. 3 illustrates a perspective view of the orthodontic bite jumping device of the present invention with the inner and outer tubes separated.
Figure 6:
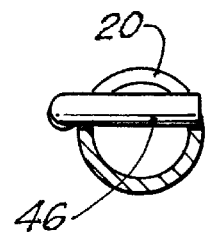
FIG. 6 illustrates a cross sectional view along the plane 3—3 of FIG. 3.
Figure 4:
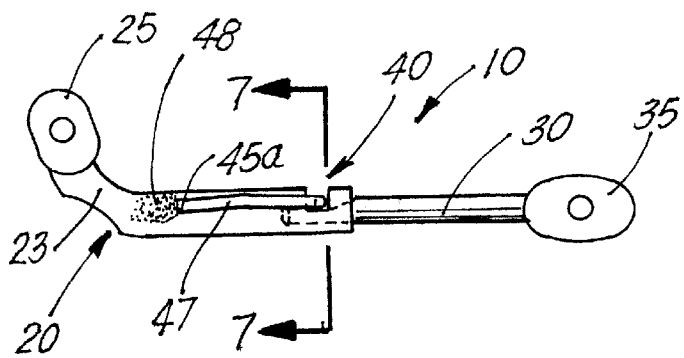
FIG. 4 illustrates a perspective view of the orthodontic bite jumping device of the present invention in the limiting position.
Figure 7:
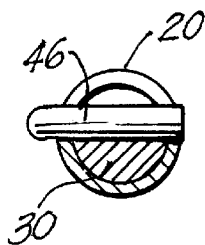
FIG. 7 illustrates a cross sectional view along the plane 4—4 of FIG. 4.
Figure 5:
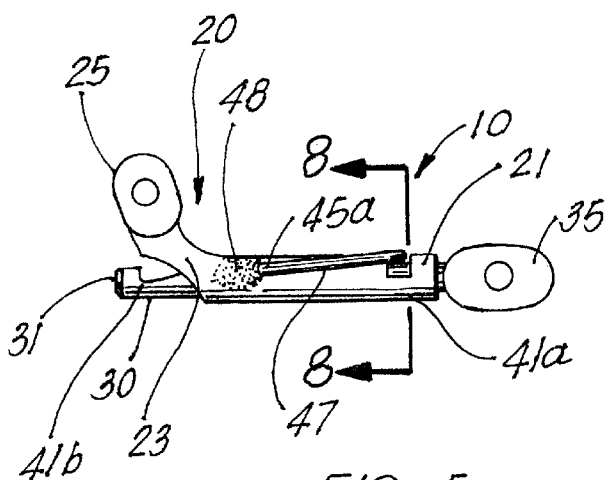
FIG. 5 illustrates a perspective view of the orthodontic bite jumping device of the present invention in a collapsed position corresponding to a closed jaw.

The telescopic tube 20 and plunger cylindrical member 30 may be secured to the maxilla (upper jaw) 2 and the mandible (lower jaw) 3, respectively, by brace wires 51, 53 (FIG. 1A and FIG. 2A) via a trunnion and threaded screw assembly 55, such as described in U.S. Pat. No. 4,462,800, issued to Jones, entitled "ORTHODONTIC BITE JUMPING DEVICE," or alternately, tooth bands 50, 52 (FIG. 1 and FIG. 2) and threaded screw assembly 55 in a manner well known in the art. In an alternate embodiment, the telescopic tube 20 and plunger cylindrical member 30 may be secured in reverse order or to the mandible (lower jaw) 3 and the maxilla (upper jaw) 2, respectively.

Figure 9:
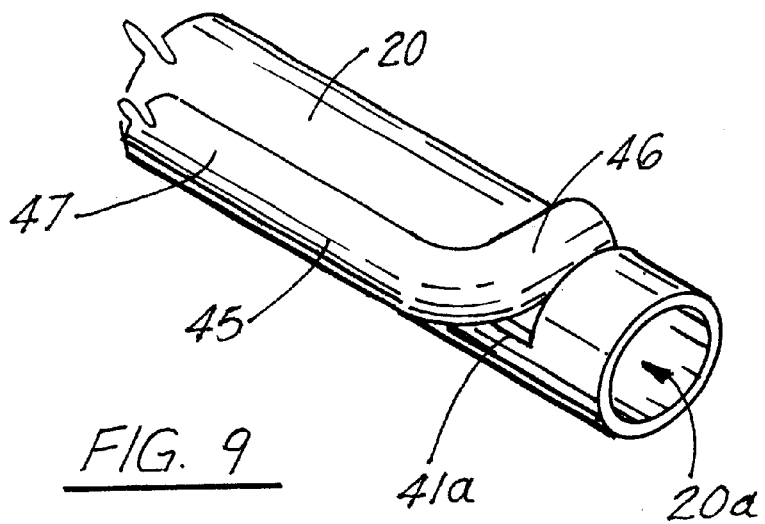
FIG. 9 illustrates a partial view of the free end of the outer tube with the L-shaped resilient lever arm of the present invention.

Referring now to FIG. 9, the L-shaped resilient lever arm 47 comprises a first leg member having a main body with a first end 45a and a second end. The main body extends along a substantial portion of the length of the telescopic or outer tube 20 to the notch 41a. The L-shaped resilient lever arm 47 further comprises a second leg member 46 perpendicular coupled to the second end and which is dimensioned to be received in the notch 41a. In the embodiment of FIGS. 1–8, the first end 45a is welded or permanently affixed to the telescopic or outer tube 20 via weld connection 48. The second leg member 46 has a length substantially equally to the diameter of the outer tube 20.

Figure 10:
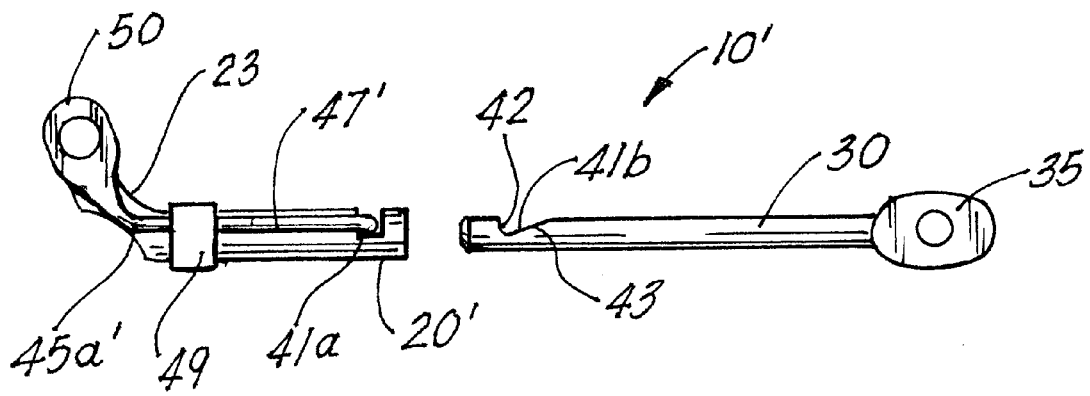
FIG. 10 illustrates a perspective view of an alternate embodiment of the orthodontic bite jumping device of the present invention with the inner and outer tubes separated.
Figure 11:
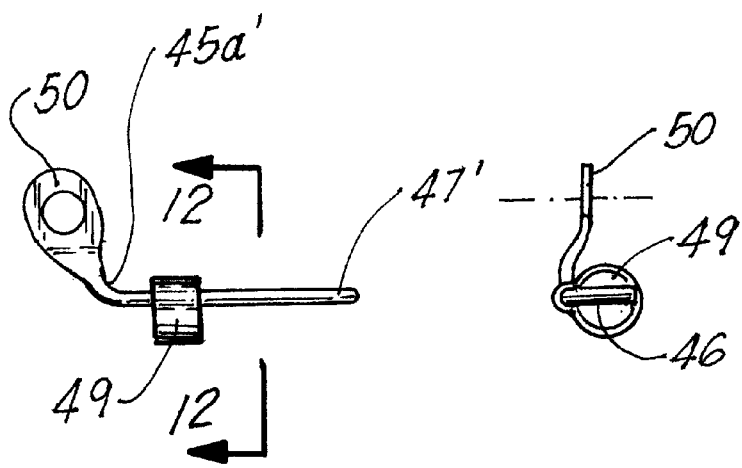
FIG. 11 illustrates a perspective view of a removable L-shaped resilient lever arm of the present invention; and, FIG. 12 illustrates a cross sectional view along the plane 11—11 of FIG. 11.
Figure 12:
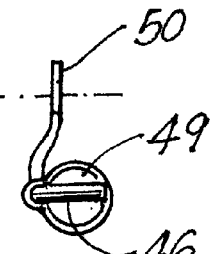

Referring now to FIGS. 10–12, a perspective view of an alternate embodiment of the orthodontic bite jumping device 10' is shown. The orthodontic bite jumping device 10' differs from the orthodontic bite jumping device 10 in that the L-shaped resilient lever arm 47' is removably coupled to the telescopic or outer tube 20' via band 49 and is secured in the manner as the telescopic or outer tube 20 via an eyelet or ring 50 coupled the first end 45a'. The eyelet or ring 50 is angularly offset from the longitudinal axis of the main body of the L-shaped resilient lever arm 47'.

In operation, the second leg member 46 of the L-shaped resilient lever arm 47 or 47' is taut in the notch 41a formed in the telescopic or outer tube 20. When the patient opens his mouth, a portion of the plunger cylindrical member 30 slides out of the central bore 20a of the telescopic or outer tube 20 or 20'. When the patient closes his mouth, a portion of the plunger cylindrical member 30 slides in the central bore 20a of the telescopic or outer tube 20 or 20'.

However, if the patient opens his mouth to an extent that the pair of notches 41a and 41b overlap, the second leg member 46 of the L-shaped resilient lever arm 47 or 47' will track the forward descending slope or ramped surface 43 until the bottom thereof or the rear tracking limiting surface 42 is engaged. Thus, the plunger or inner cylindrical member 30 is prevented from being pulled out of the central bore 20a of the telescopic or outer tube 20 or 20'.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. An orthodontic bite jumping device comprising
   an outer tube having one end adapted to be mounted to an upper jaw;
   an inner cylindrical member concentrically disposed in said outer tube and adapted to be mounted to a lower jaw; and,
   a telescoping limiting assembly which limits the distance said inner cylindrical member can slide out of said outer tube, said telescoping limiting assembly includes:
   a first notch formed in close proximity to a free end of said outer tube,
   a second notch formed in close proximity to a free end of said inner cylindrical member and having a rear blocking surface and a forward descending slope or ramped surface sloped to a bottom of said rear blocking surface and,
   an L-shaped resilient lever arm which tracks along a top of said inner cylindrical member in the first notch and tracks along the forward descending slope or ramped surface to said rear blocking surface as a portion of said inner cylindrical member slides out of said outer tube.

2. The device of claim 1, wherein said L-shaped resilient lever arm resiliently tracks along the forward descending slope or ramped surface out of said second notch as said portion of said inner cylindrical member slides into said outer tube.

3. The device of claim 1, wherein said L-shaped resilient lever arm comprises:
   a first leg member having a main body with a first end and a second end, said main body extending along a substantial portion of the length of the outer tube to said first notch;
   a second leg member perpendicularly coupled to the second end dimensioned to be received in said first notch;
   an eyelet or ring coupled to said first end and angularly offset from the longitudinal axis of said main body; and
   a band for securing said main body onto said outer tube.

4. The device of claim 3, wherein said second leg member has a length substantially equal to the diameter of the outer tube.

5. The device of claim 1, wherein said L-shaped resilient lever arm comprises:
   a first leg member having a main body with a first end and a second end, said main body extending along a substantial portion of the length of the outer tube to said first notch wherein said first end is permanently affixed to said outer tube;
   a second leg member perpendicularly coupled to the second end dimensioned to be received in said first notch.

6. The device of claim 5, wherein said first end of said main body is permanently affixed to said outer tube via a welded connection.

7. The device of claim 1, wherein said L-shaped resilient lever arm, said outer tube and said inner cylindrical member are made of a metal.

8. The device of claim 1, wherein:
   said one end of said outer tube comprises an angularly offset ring or eyelet having a thin width;
   a first threaded screw adapted to be received in said ring or said eyelet of said one end of said outer tube;
   means for connecting said first threaded screw to at least one tooth of said upper jaw;
   one end of said inner cylindrical member comprises a ring or eyelet having a thin width;
   a second threaded screw adapted to be received in said ring or said eyelet of said one end of said inner cylindrical member;

means for connecting said second threaded screw to at least one tooth of said lower jaw.

9. The device of claim 8, wherein said angularly offset ring or, eyelet is offset by approximately 45 degrees from a longitudinal axis of said outer tube.

10. An artificial orthodontic joint for connection between a maxilla and a mandible comprising:
   a telescopic tube having one end adapted to be mounted to said maxilla;
   a first notch formed in close proximity to a free end of said telescopic tube;
   a plunger cylindrical member concentrically disposed in said telescopic tube and adapted to be mounted to said mandible;
   a second notch formed in close proximity to a free end of said plunger cylindrical member and having a rear tracking limiting surface and a forward descending slope or ramped surface sloped to and ending at a bottom of said rear tracking limiting surface; and,
   an L-shaped resilient lever, arm coupled to said telescopic tube and which tracks along a top of said plunger cylindrical member in the first notch and along the forward descending slope or ramped surface as a portion of said plunger moves out of said telescopic tube.

11. The joint of claim 10, wherein said L-shaped resilient lever arm resiliently tracks along the forward descending slope or ramped surface out of said second notch as said portion of said plunger cylindrical member slides into said telescopic tube.

12. The joint of claim 10, wherein said L-shaped resilient lever arm is removable and comprises:
   a first leg member having a main body with a first end and a second end, said main body extending along a substantial portion of the length of the telescopic tube to said first notch;
   a second leg member perpendicularly coupled to the second end dimensioned to be received in said first notch;
   an eyelet or ring coupled to said first end and angularly offset from the longitudinal axis of said main body; and
   a band for securing said main body onto said telescopic tube.

13. The joint of claim 12, wherein said second leg member has a length substantially equal to the diameter of the telescopic tube.

14. The joint of claim 11, wherein said L-shaped resilient lever arm is integral with said telescopic tube and comprises:
   a first leg member having a main body with a first end and a second end, said main body extending along a substantial portion of the length of the telescopic tube to said first notch wherein said first end is permanently affixed to said telescopic tube;
   the second leg member perpendicularly coupled to a second end dimensioned to be received in said first notch.

15. The joint of claim 14, wherein said first end of said main body is permanently affixed to said telescopic tube via a welded connection.

16. The joint of claim 10, wherein said L-shaped resilient lever arm, said telescopic tube and said plunger cylindrical member are made of a metal.

17. The joint of claim 10, wherein:
   said one end of said telescopic tube comprises an angularly offset ring or eyelet having a thin width;
   a first threaded screw adapted to be received in said ring or said eyelet of said one end of same telescopic tube;
   means for connecting said first threaded screw to at least one tooth of said maxilla;
   one end of said plunger cylindrical member comprises a ring or eyelet having a thin width;
   a second threaded screw adapted to be received in said ring or said eyelet of said one end of said plunger cylindrical member;
   means for connecting said second threaded screw to at least one tooth of said mandible.

18. The joint of claim 17, wherein said angularly offset ring or eyelet is offset by approximately 45 degrees from a longitudinal axis of said telescopic tube.

19. An artificial orthodontic joint for connection between a maxilla and a mandible comprising:
   a telescopic tube having one end adapted to be mounted to said mandible;
   a first notch formed in close proximity to a free end of said telescopic tube;
   a plunger cylindrical member concentrically disposed in said telescopic tube and adapted to be mounted to said maxilla;
   a second notch formed in close proximity to a free end of said plunger cylindrical member and having a rear tracking limiting surface and a forward descending slope or ramped surface sloped to and ending at a bottom of said rear tracking limiting surface; and,
   an L-shaped resilient lever arm coupled to said telescopic tube and which tracks along a top of said plunger cylindrical member in the first notch and along the forward descending slope or ramped surface as a portion of said plunger moves out of said telescopic tube.

20. The joint of claim 19, wherein said L-shaped resilient lever arm resiliently tracks along the forward descending slope or ramped surface out of said second notch as said portion of said plunger cylindrical member slides into said telescopic tube.

* * * * *